US007919525B2

(12) United States Patent
Kumar et al.

(10) Patent No.: US 7,919,525 B2
(45) Date of Patent: Apr. 5, 2011

(54) RADIATION PROTECTION BY GAMMA-TOCOTRIENOL

(75) Inventors: K. Sree Kumar, Rockville, MD (US); Venkataraman Srinivasan, Germantown, MD (US); Thomas M. Seed, Bethesda, MD (US); Andreas Papas, Jonesborough, TN (US)

(73) Assignee: Henry M. Jackson Foundation for the Advancement of Military Medicine, Inc., Rockville, MD (US)

( * ) Notice: Subject to any disclaimer, the term of this patent is extended or adjusted under 35 U.S.C. 154(b) by 485 days.

(21) Appl. No.: 10/545,674

(22) PCT Filed: Feb. 17, 2004

(86) PCT No.: PCT/US2004/004522
§ 371 (c)(1),
(2), (4) Date: Apr. 27, 2006

(87) PCT Pub. No.: WO2004/086412
PCT Pub. Date: Oct. 7, 2004

(65) Prior Publication Data
US 2006/0247306 A1    Nov. 2, 2006

Related U.S. Application Data

(60) Provisional application No. 60/447,298, filed on Feb. 14, 2003.

(51) Int. Cl.
*A61K 31/355* (2006.01)
(52) U.S. Cl. ...................................................... 514/458
(58) Field of Classification Search .................. 514/458
See application file for complete search history.

(56) References Cited

U.S. PATENT DOCUMENTS

| 5,376,361 | A | 12/1994 | Perricone |
| 5,709,868 | A * | 1/1998 | Perricone ............ 424/401 |
| 5,840,734 | A | 11/1998 | Bernstein |
| 6,251,878 | B1 | 6/2001 | Strickland et al. |
| 6,716,451 | B1 * | 4/2004 | Udell et al. ............ 424/455 |
| 7,449,451 | B2 * | 11/2008 | Prasad et al. .......... 514/52 |
| 2003/0064955 | A1 * | 4/2003 | Prasad et al. .......... 514/52 |

FOREIGN PATENT DOCUMENTS

| CN | 1178675 | * | 4/1998 |
| DE | 4405545 | * | 8/1995 |
| FR | 2781156 | A1 | 1/2000 |
| JP | 05213763 | * | 8/1993 |
| JP | 2002-521321 | T | 7/2002 |
| JP | 2002-332231 | A | 11/2002 |
| WO | 03/039452 | | 5/2003 |

OTHER PUBLICATIONS

Jarrett et al. (Radiation Measurements 42(6-7) 2007, 1063-1074).*
Karjala, My battle with stage IV lung cancer, 23 pages, 2000.*
Blumenthal et al Proceedings of the American association for Cancer Research, Abstract, vol. 40, #4227, Mar. 1999.*
Moss (1981), International Union of Pure and Applied Chemistry, 6 pages.*
Clinical trials, 2005, 4 pages.*
Weiss, Environmental Health Perspectives 15(6) 1473-1478, (1997).*
Moller , The FASEB J. 16, 45-53, (2002).*
Ross et al. Scanning Microsc (1990) Abstract Only.*
Weber, et al., "Efficacy of Topically Applied Tocopherols and Tocotrienols in Protection of Murine Skin From Oxidative Damage Induced by UV-Irradiation", Free Radical Biology and Medicine, vol. 22, No. 5, pp. 761-769, Abstract only, 1997.
Kamal-Eldin, et al., "The Chemistry and Antioxidant Properties of Tocopherols and Tocotrienols," Lipids, vol. 31, No. 7, pp. 671-701 (1996).
Ahn, et al., "γ-tocotrienol inhibits nuclear factor-κB signaling pathway through inhibition of receptor-interacting protein and TAK1 leading to suppression of antiapoptotic gene products and potentiation of apoptosis," Journal of Biological Chemistry, vol. 282, No. 1, pp. 809-820 (2007).
Singh, et al., "Induction of Cytokines by Radioprotective Tocopherol Analogs," Experimental and Molecular Pathology, vol. 81, pp. 55-61 (2006).
Sen, et al., "Tocotrienols: Vitamin E beyond tocopherols," Life Sciences, vol. 78, pp. 2088-2098 (2006).
Supplementary European Search Report, dated Oct. 10, 2007, issued in European application No. 04711839.3.
Journal of Pharmacological Sciences, "The effect of vitamin E analogs against $H_2O_2$-induced neurotoxin in striate body," 117(2):33, (Feb. 1, 2001), partial translation (1 page).
Kamat et al. "Tocotrienols from palm oil as potent inhibitors of lipid peroxidation and protein oxidation in rat brain mitochondria," Neuroscience Letters, 195:179-182 (1995) (4 pages).
Podda et al., "A combination of vitamin E homologues applied to skin protects against ultraviolet-irradiation-induced damage," Dept. Molecular and Cell Biology, University of California Berkeley, 106(4):919 (Apr. 1996) (1 page).
Sugiyama et al., "Effect of vitamin E on cytotoxicity, DNA single strand breaks, chromosomal aberrations, and mutation in Chinese hamster V-79 cells exposed to ultraviolet-B light," Photochemistry and Photobiology, 56(1):31-34 (1992) (4 pages).
Kumar, et al., "Nutritional Approaches to Radioprotection: Vitamin E", Military Medicine, 167 Suppl., 1:57-59 (2002) (5 pages).

* cited by examiner

*Primary Examiner* — Brandon J Fetterolf
*Assistant Examiner* — Shirley V Gembeh
(74) *Attorney, Agent, or Firm* — Wilmer Cutler Pickering Hale and Dorr LLP

(57) ABSTRACT

The present invention relates to methods for the prevention and treatment of a mammal from radiation-induced internal injury using γ-tocotrienol, α-tocopherol succinate or γ-tocotrienol succinate. Specifically, the present invention relates to methods for preventing and treating radiation-induced injuries in a mammal by (1) subcutaneous, intramuscular, intraperitoneal, or intravascular injection of a therapeutically effective amount of γ-tocotrienol; or (2) oral administration of a therapeutically effective amount of α-tocopherol succinate or γ-tocotrienol succinate or both.

11 Claims, 6 Drawing Sheets

RADIATION PROTECTION BY GAMMA-TOCOTRIENOL

This application claims priority from U.S. Provisional Application Ser. No. 60/447,298 filed Feb. 14, 2003. The entirety of that provisional application is incorporated herein by reference.

This invention was made with United States Government support. The Government may have certain rights in the invention.

FIELD OF THE INVENTION

The present invention is directed to a method of using tocotrienol and tocopherol compounds as radioprotectants for the prevention and treatment of radiation-induced internal injury and mortality in mammals.

BACKGROUND OF THE INVENTION

Ionizing radiation is an electromagnetic or particulate radiation capable of producing ion pairs by interaction with matter. Typical ionizing radiation includes X-rays, gamma rays, alpha particles, beta particles (electrons), neutrons, and charged nuclei. In humans, excessive radiation-induced hazards range from short term mortality (when exposed to lethal doses of radiation) to long term pathologies including carcinogenesis (when exposed to low levels of radiation over an extended period of time). Exposure to damaging or lethal ionizing radiation may occur in a variety of ways, such as in therapeutic radiology, nuclear power plant accidents, disposal of nuclear waste materials, outer space explorations by astronauts, and the potential use of nuclear weapons by terrorists or belligerent nations. Exposure from many of these situations are predictable, and therefore, modalities of prevention play an important role in radiation protection. For example, the radiation dose that is used to kill tumor tissue in a radiotherapy of cancer is now limited because of the possible lethality of normal tissue associated with higher doses. The consequences of these exposures depend upon the degree of exposure to radiation and may vary from absence of any discernable immediate effect to long-term and short-term mortality. Even though there may not be any discernable immediate or short-term effects in cases of low-level exposures, the effects may be expressed as late arising pathologies like cancer.

Although extensive research has been carried out both at the government and private sector level, only a very few drugs were identified to be effective in preventing radiation damage. These drugs, however, all have undesirable side effects that prevented their use in humans. Thus, there is still a need for a composition which is proven effective and safe in the prevention and treatment of radiation damage in humans.

In recent years, it has been recognized that the presence of free radicals may cause severe damage to the human body, since the free radicals react with important cellular components, such as DNA or the cell membrane, to diminish or impair critical cellular functions. For instance, oxygen-free radicals are implicated in many diseases including neurodegenerative diseases (ALS, Parkinson's, Alzheimer's), cataractogenesis, atherosclerosis, diabetes mellitus, ischemia-reperfusion injury, kwashiorkor, and certain toxicities, to mention only a few.

Free-radicals may be neutralized by antioxidants. One of the nutritionally provided antioxidants is vitamin E ($\alpha$-tocopherol), a lipophilic oily substance that can break or prevent the propagation of free radicals in biological systems. Since radiation damage is mediated through radiation-induced free radicals, vitamin E has been used for the protection from radiation induced injuries.

For example, Weber et al [*Free Radical Biology & Medicine*, 22:761-769, (1997)] investigated the efficacy of topically applied tocopherols and tocotrienols in the protection of murine skin from oxidative damage induced by UV irradiation. In particular, a tocotrienol rich fraction of palm oil (TRF) was applied to mouse skin and the content of antioxidants (i.e., $\alpha$ and $\gamma$ tocopherol as well as $\alpha$ and $\gamma$ tocotrienol) before and after exposure to UV-light were measured. Weber found that prior application of the TRF to mouse skin resulted in the preservation of vitamin E in the skin [Weber et al., supra, (1997)].

U.S. Pat. No. 5,376,361 also describes a method for the prevention and/or treatment of radiation induced skin damage. The method comprises topically applying a tocotrienol or a vitamin E preparation enriched with tocotrienol to the skin. However, vitamin E is less effective as a radioprotectant when used internally.

SUMMARY OF THE INVENTION

The present invention is directed to a method for the prevention and treatment of radiation-induced internal damage in a mammal, the method comprising administering to the mammal a therapeutically effective amount of a pharmaceutical composition comprising at least one of $\gamma$-tocotrienol, $\alpha$-tocopherol succinate, and $\gamma$-tocotrienol succinate. One aspect of the present invention relates to methods for preventing a mammal from radiation-induced internal damages, such as the suppression of the hematopoietic system, by administering the mammal a therapeutically effective amount of $\gamma$-tocotrienol, $\alpha$-tocopherol succinate or $\gamma$-tocotrienol succinate.

Another aspect of the present invention relates to methods for treating a mammal suffering from radiation-induced damages by administering the mammal a therapeutically effective amount of $\gamma$-tocotrienol, $\alpha$-tocopherol succinate or $\gamma$-tocotrienol succinate.

In one embodiment, the $\gamma$-tocotrienol is injected into a mammal subcutaneously, intramuscularly, intraperitoneally, or intravascularly to prevent or treat radiation-induced damage.

In another embodiment, the $\alpha$-tocopherol succinate or $\gamma$-tocotrienol succinate or both are given by oral administration to a mammal to prevent or treat radiation induced damage. The $\alpha$-tocopherol succinate or $\gamma$-tocotrienol succinate or both can also be injected subcutaneously, intramuscularly, intraperitoneally, or intravascularly into a mammal.

DETAILED DESCRIPTION OF THE INVENTION

Figure 1:
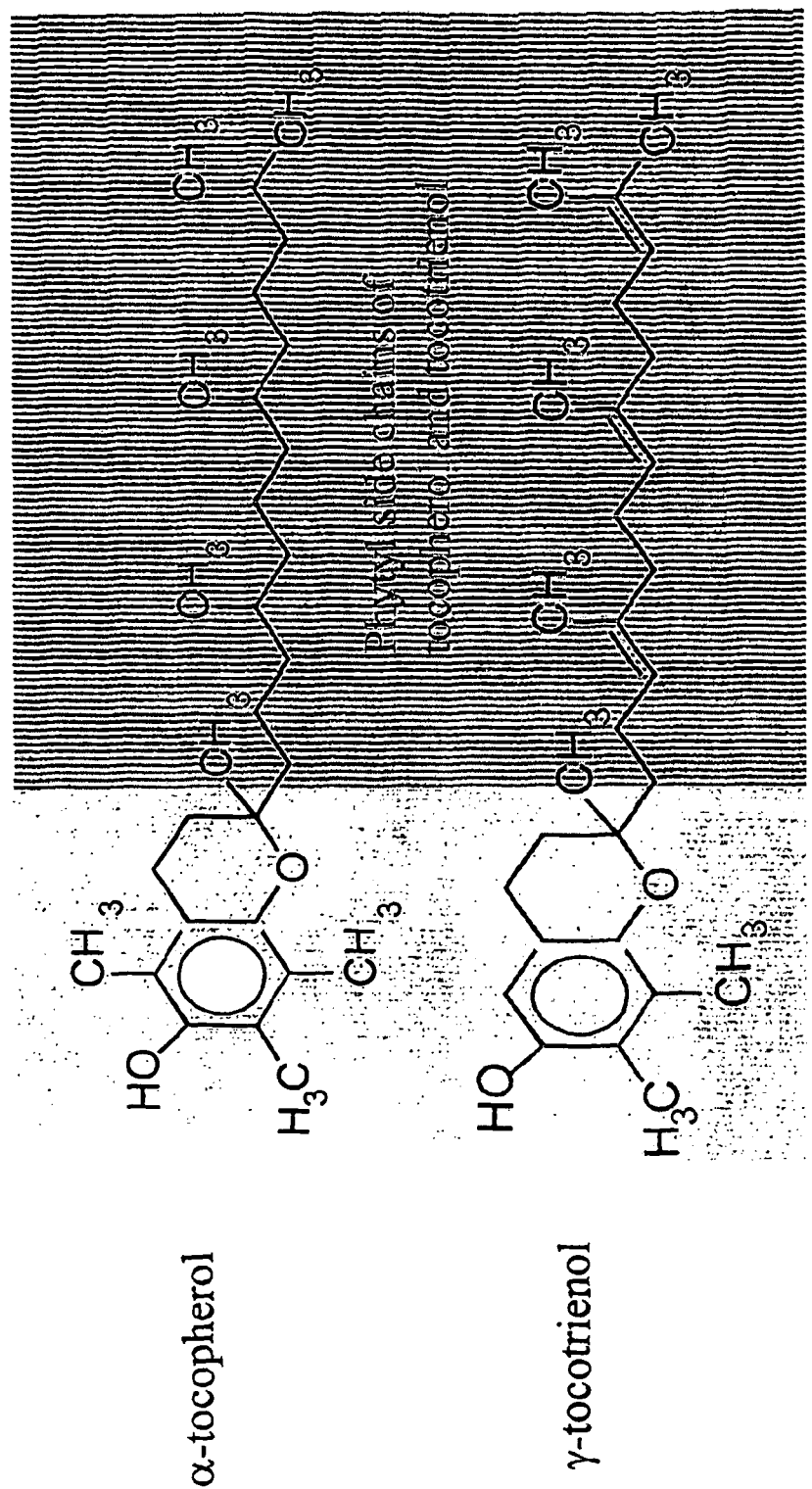
FIG. 1 is a comparison of chemical structures between $\gamma$-tocotrienol and $\alpha$-tocopherol. The side chain of $\gamma$-tocotrienol is unsaturated and its phenyl ring has an additional methyl group.

The primary objective of the present invention is to provide methods for the prevention of a mammal who is at risk of radiation-induced lethality. Another objective of the present invention is to provide a treatment for a mammal from radiation-induced internal damages. The third objective of the present invention is to use tocotrienol compounds for the specific purpose of minimizing the side effects of radiation exposure in non-cancerous tissue during radiotherapy for cancer treatment. The side effects from radiotherapy may be minimized and/or the efficacy of radiotherapy may be enhanced by administration of tocotrienol compounds. The present invention is particularly useful for the prevention and/or to treatment of radiation-induced suppression of the hematopoietic system, as well as other damages.

One embodiment of the present method comprises injecting a mammal a therapeutically effective amount of tocotrienol, or a derivative thereof (hereinafter referred to collectively as "tocotrienol" for ease of reference).

The term "tocotrienol" encompasses counterparts of tocopherol (vitamin E) that bear unsaturated tails, and include, but not limited to, α-, β-, γ-, and δ-tocotrienols, desmethyl-tocotrienol, didesmethyl-tocotrienol (occurring in sunflower seeds, vegetable oils, barley, brewer's grains, oats, and African violets), their synthetic counterparts, their counterparts having methylated or demethylated chroman rings, and mixtures thereof. The double bonds may be cis or trans or mixtures thereof. As described earlier, the term "tocotrienol" also encompasses tocotrienol derivatives.

In many embodiments utilizing tocotrienol in the composition, the tocotrienol is isolated from natural sources. However, synthetic preparations may also be employed as well as mixtures of natural and synthetic tocotrienol. Useful tocotrienols are natural products isolated from, for example, wheat germ oil, bran, or palm oil using high performance liquid chromatography, or isolated by alcohol extraction and/or molecular distillation from barley, brewer's grain or oats. As used herein, the term "tocotrienols" includes tocotrienol-rich-fractions obtained from these natural products as well as the pure compounds. Where tocotrienol derivatives are employed, they must be functionally equivalent to tocotrienol. Preferred derivatives contain both the chromanol nucleus and three double bonds in the hydrocarbon tail.

Generally, the tocotrienol is injected subcutaneously, intramuscularly, intraperitoneally, or intravascularly.

In a preferred embodiment of the invention, the tocotrienol is γ-tocotrienol or its derivative.

In another preferred embodiment of the present invention, the tocotrienol is applied in admixture with a pharmaceutically acceptable carrier to facilitate absorption after injection.

Pharmaceutical carriers suitable for injectable use include sterile solutions or dispersions for the extemporaneous preparation of sterile injectable solutions or dispersion. In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., tocotrienol or tocotrienol enriched Vitamin E) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above.

Another embodiment of the present invention comprises orally administering to a mammal a therapeutically effective amount of tocopherol succinate or tocotrienol succinate.

In a preferred embodiment, the tocopherol succinate is α-tocopherol succinate.

In another preferred embodiment, the tocotrienol succinate is γ-tocotrienol succinate.

In yet another preferred embodiment, the tocopherol succinate or tocotrienol succinate is administered in an oral composition.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier, wherein the compound in the fluid carrier is applied orally and swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or stearates; a glidant such as colloidal silicon dioxide; a sweetening agent such as sucrose or saccharin; or a flavoring agent such as peppermint, methyl salicylate, or orange flavoring.

Another embodiment for the prevention or treatment of radiation-induced damage of the present invention comprises administering to a mammal a therapeutically effective amount of tocopherol succinate or tocotrienol succinate by subcutaneous, intramuscular, intraperitoneal, or intravascular injection.

It is especially advantageous to formulate compositions in dosage unit form for ease of administration and uniformity of dosage. Dosage unit form as used herein includes physically discrete units suited as unitary dosages for the subject to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that includes the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Another aspect of the present invention provides for both prophylactic and therapeutic methods of treating a mammal at risk for, susceptible to or diagnosed with radiation-associated tissue damage. In one embodiment, the invention provides a method for preventing a mammal from radiation-associated internal damage, by administering to the mammal a therapeutically effective amount of a pharmaceutical composition containing tocopherol or tocotrienol. In another embodiment, the invention provides a method for treating in a mammal radiation-associated internal damage, by administering to the mammal a therapeutically effective amount of the pharmaceutical composition.

The effective amount of tocotrienol, tocopherol, tocotrienol succinate or tocopherol succinate necessary to bring about prevention and/or therapeutic treatment of radiation-induced damage is not fixed per se. A therapeutically effective amount is necessarily dependent upon the identity and form of tocotrienol, tocopherol, tocotrienol succinate or tocopherol succinate employed, the extent of the protection needed, or the severity of the radiation damage to be treated.

Administration of the pharmaceutical composition can occur prior to the exposure to radiation, such that radiation-associated internal damage is prevented or, alternatively, delayed in its progression. The appropriate dose and route of administration of the pharmaceutical composition can be determined based on the level of radiation exposure or potential risk of radiation.

With regard to both prophylactic and therapeutic methods of treatment, such treatments may be specifically tailored or modified, based on knowledge obtained from the field of pharmacogenomics. "Pharmacogenomics," as used herein, includes the application of genomics technologies such as gene sequencing, statistical genetics, and gene expression analysis to drugs in clinical development and on the market. More specifically, the term refers to the study of how a subject's genes determine his or her response to a drug (e.g., a subject's "drug response phenotype" or "drug response genotype"). Thus, another aspect of the invention provides methods for tailoring an individual's prophylactic or therapeutic treatment with the pharmaceutical composition according to that individual's drug response. Pharmacogenomics allows a clinician or physician to target prophylactic or therapeutic treatments to subjects who will most benefit from the treatment and to avoid treatment of subjects who will experience toxic drug-related side effects.

Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining, for example, whether to administer amifostine and vitamine E as well as tailoring the dosage and/or therapeutic regimen of treatment with amifostine and vitamine E.

Pharmacogenomics deals with clinically significant hereditary variations in the response to drugs due to altered drug disposition and abnormal action in affected persons. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is hemolysis after ingestion of oxidant drugs (anti-malarials, sulfonamides, analgesics, nitrofurans) and consumption of fava beans.

One pharmacogenomics approach to identifying genes that predict drug response, known as "a genome-wide association," relies primarily on a high-resolution map of the human genome consisting of already known gene-related sites (e.g., a "bi-allelic" gene marker map which consists of 60,000-100,000 polymorphic or variable sites on the human genome, each of which has two variants). Such a high-resolution genetic map can be compared to a map of the genome of each of a statistically substantial number of subjects taking part in a Phase II/III drug trial to identify genes associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process. However, the vast majority of SNPs may not be disease associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach," can be utilized to identify genes that predict drug response. According to this method, if a gene that encodes a drug target is known, all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some subjects do not obtain the expected drug effects or show exaggerated drug response and serious toxicity after taking the standard and safe dose of a drug. These polymorphisms are expressed in two phenotypes in the population, the extensive metabolizer and poor metabolizer. The prevalence of poor metabolizer phenotypes is different among different populations. For example, the gene coding for CYP2D6 is highly polymorphic and several mutations have been identified in poor metabolizers, which all lead to the absence of functional CYP2D6. Poor metabolizers of CYP2D6 and CYP2C19 quite frequently experience exaggerated drug response and side effects when they receive standard doses. If a metabolite is the active therapeutic moiety, poor metabolizers show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling" can be utilized to identify genes that predict drug response. For example, the gene expression of an animal dosed with a drug (e.g., gene expression in response to amifostine) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with radiation-protective tocopherol or tocotrienol.

Modifications to the above-described compositions and methods of the invention, according to standard techniques, will be readily apparent to one skilled in the art and are meant to be encompassed by the invention.

The protection from radiation-induced lethality by tocotrienol, tocopherol succinate, and tocotrienol succinate is demonstrated in the following examples. Although the results are presented here for mice, tocotrienol and tocopherol have been used as a nutritional supplement in humans and hence can be directly applicable to human scenarios.

The present invention is further illustrated by the following examples which should not be construed as limiting. The contents of all references, patents and published patent applications cited throughout this application, as well as the Figures and Tables are incorporated herein by reference.

EXAMPLE 1

Animals

CD2F1 male mice, 6-8 weeks old (approximately 25 g), procured from Jackson Labs were used throughout this study and were kept in rooms maintained at 21±0.5° C. Animals on arrival were maintained in quarantine for 10 days during which time serological testing was done for contamination by pathogens. All animals were provided with pellet diet and water ad lib.

EXAMPLE 2

Preparation of γ-tocotrienol

A preparation of γ-tocotrienol in a final volume of 1 ml was made by mixing 0.11 ml of γ-tocotrienol with 0.85 ml PEG-400 (polyethylene glycol-400) and 0.05 ml of vital-E-placebo, a solubilizing agent (Schering-Plough). 1 ml of the preparation is sufficient for 8 mice. Final concentration of γ-tocotrienol is 100 mg/ml. Vehicle for injection into control animals was prepared exactly as for γ-tocotrienol except that 0.11 ml of olive oil was used instead of γ-tocotrienol.

EXAMPLE 3

Injection of Animals and Radiation

Each animal was injected subcutaneously (at the nape of the neck) with 0.1 ml of either γ-tocotrienol or vehicle preparation. Injections were done 20-24 hours before irradiation.

Animals were placed in well-ventilated Lucite boxes (8 animals in a compartmentalized box) and irradiated in a Cobalt-60 facility at a radiation dose rate of 0.6 Gy/min for a total radiation dose of 10.5 and 11 Gy. The radiation dose used is a super lethal dose. The LD50/30 radiation dose for this strain of mice is 8.9 Gy with the vehicle alone. The radiation dose and dose rate were the same that had been used for α-tocopherol studies.

EXAMPLE 4

Monitoring for Efficacy of γ-tocotrienol

After radiation, mice were returned to their original cages with free access to food and water. Mice were weighed and monitored for survivors everyday for 30 days. Percentages of survivors at the end of 30 days are used as a measure of the efficacy of γ-tocotrienol in protecting from radiation damage.

EXAMPLE 5

Efficacy of γ-tocotrienol as a Radioprotectant

Figure 2:
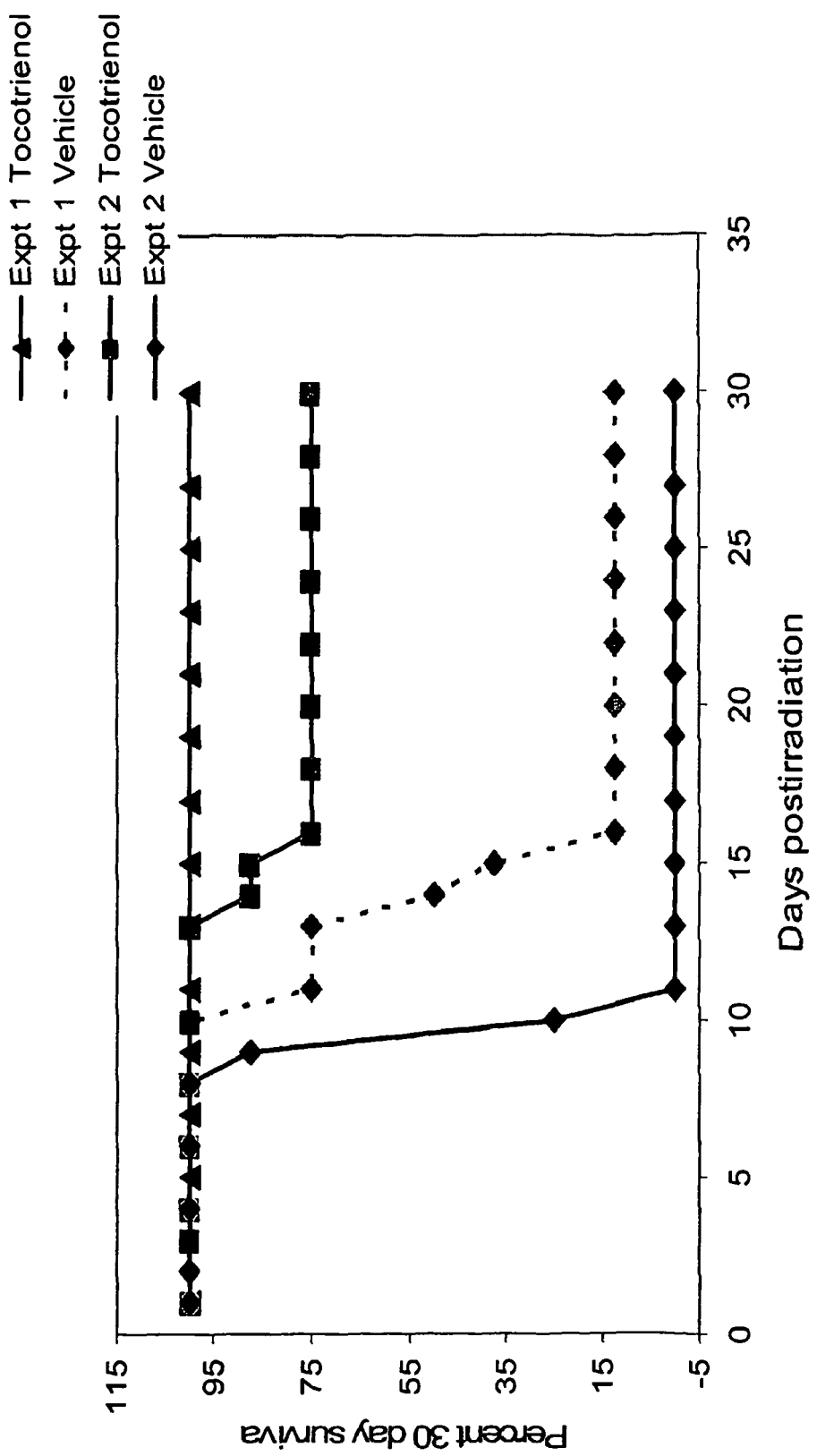
FIG. 2 shows radioprotection by $\gamma$-tocotrienol in two different experiments. In experiment 1, there was 100% survival on exposure to 10.5 Gy after $\gamma$-tocotrienol injection while only 12.5% of controls survived. In experiment 2, there was 75% survival in $\gamma$-tocotrienol treated animals and none of the controls survived.

Two experiments were done with eight animals in each experiment. As shown in FIG. 2, in Experiment 1, 100% of animals, who were treated with γ-tocotrienol survived 10.5 Gy radiation, but only 12.5% of the vehicle treated animals survived. In Experiment 2, 75% of the animals treated with γ-tocotrieriol were protected from radiation lethality and there were no survivors in the vehicle treated group.

EXAMPLE 6

Comparison of the Efficacy of γ-tocotrienol with α-tocopherol

Figure 3:
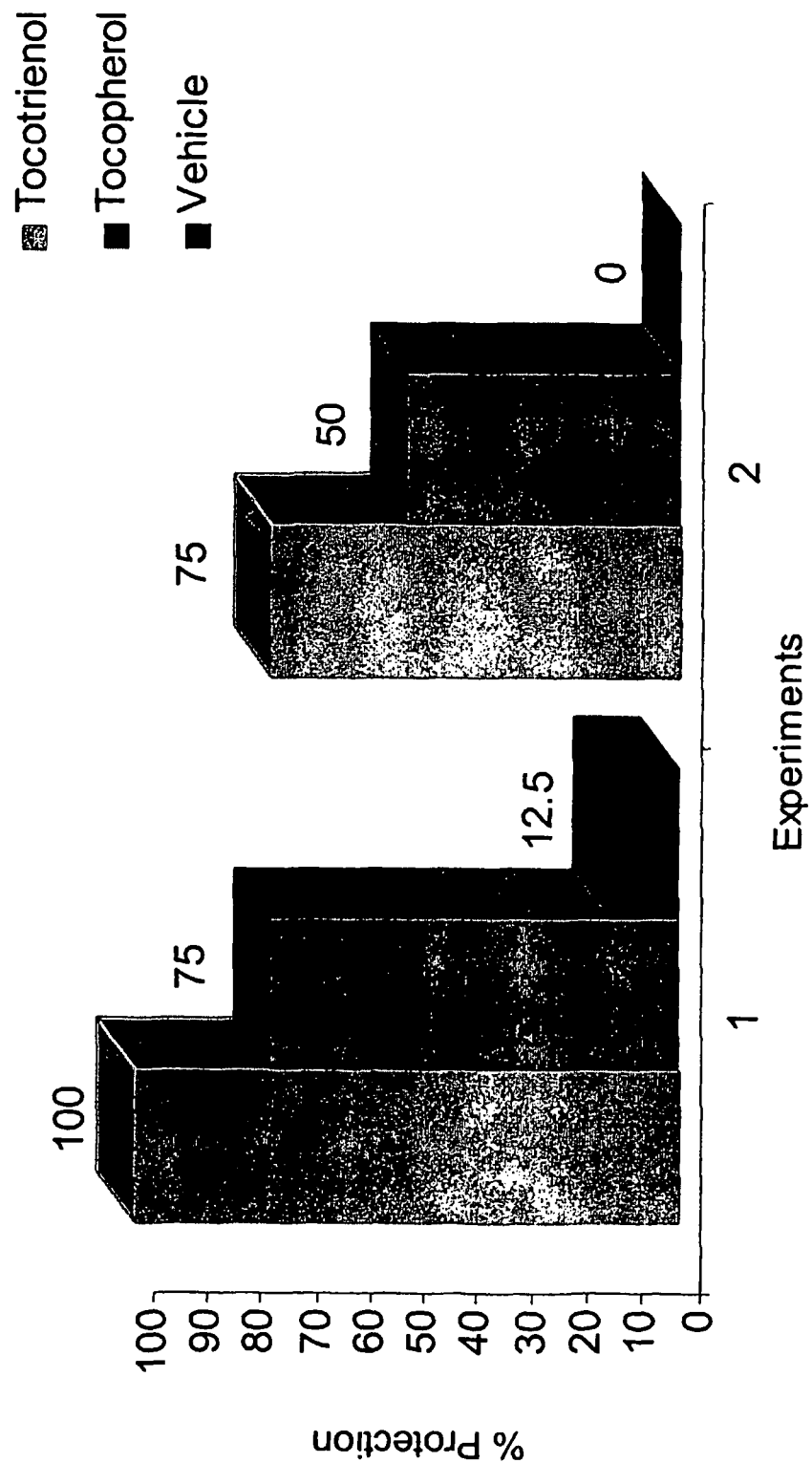
FIG. 3 is a comparison of the survival-protection efficacies of $\gamma$-tocotrienol with that of $\alpha$-tocopherol, an analogue of $\gamma$-tocotrienol is at 10.5 Gy with 0.6 Gy per minute. In two experiments, $\gamma$-tocotrienol provided 100% and 75% survival-protection from radiation, whereas α-tocopherol provided only 75 and 50% respectively at these two experiments.

The efficacies of the two isomers were compared and the results are shown in FIG. 3. A radiation dose of 10.5 Gy was used in both cases and two experiments were done with 8 mice in each experiment. Protection by γ-tocotrienol was consistently higher by 25% in both experiments. γ-tocotrienol protected 100% and 75% and α-tocopherol provided 75% and 50% protection respectively. Vehicle did not have any effect or had only very small effect.

EXAMPLE 7

Protective Efficacy of γ-tocotrienol at Higher Radiation Dose

Figure 4:
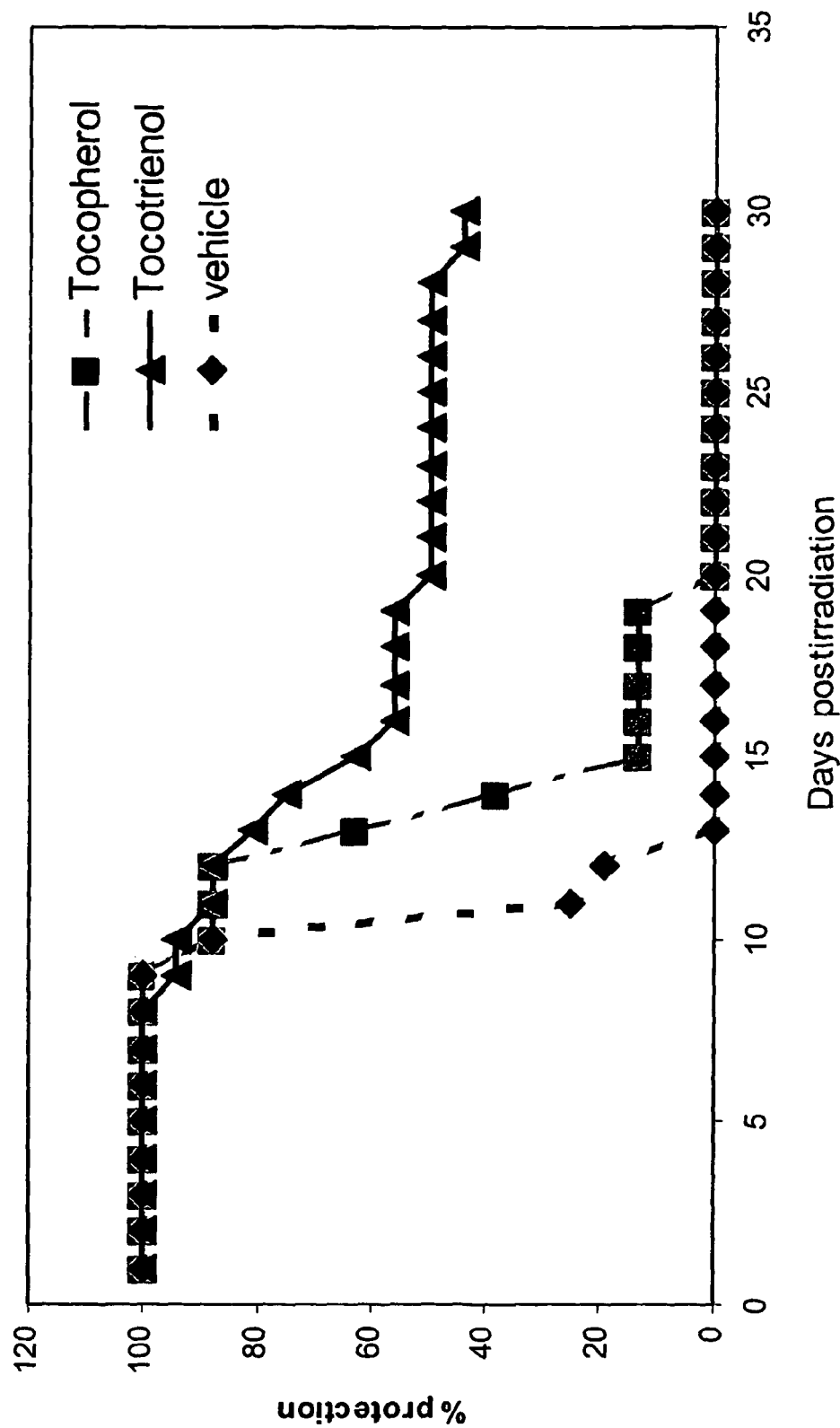
FIG. 4 is a comparison of efficacies of γ-tocotrienol and α-tocopherol at higher radiation dose of 11 Gy. At this high radiation dose even α-tocopherol was not effective, whereas with γ-tocotrienol 40% animals survived.

Since both α-tocopherol and γ-tocotrienol were protective at 10.5 Gy, a higher radiation dose of 11 Gy was used to distinguish between these two isomers in their protective efficacies. FIG. 4 compares the efficacies at a radiation dose of 11 Gy and shows γ-tocotrienol is a better radioprotectant than α-tocopherol even at a such high radiation dose.

When animals (mice) are exposed to 8.5 Gy of Cobalt radiation, about 50% of the animals die in 30 days. When the radiation dose is increased to 10.5 Gy there is either no survivors or only a few (less than 15%) survivors. However, when the animals were given γ-tocotrienol before irradiation, 75%-100% of the animals survived. Protection from the parent compound, α-tocopherol was only 25% less than that of γ-tocotrienol. When the radiation dose was further raised to 11 Gy, there was no survivors even with α-tocopherol, but 40% of the animals treated with γ-tocotrienol survived. Thus the use of γ-tocotrienol can increase the number of survivors from a nuclear exposure.

EXAMPLE 8

γ-tocotrienol Treatment Restores the Loss of Body Weight After Radiation

Figure 5:
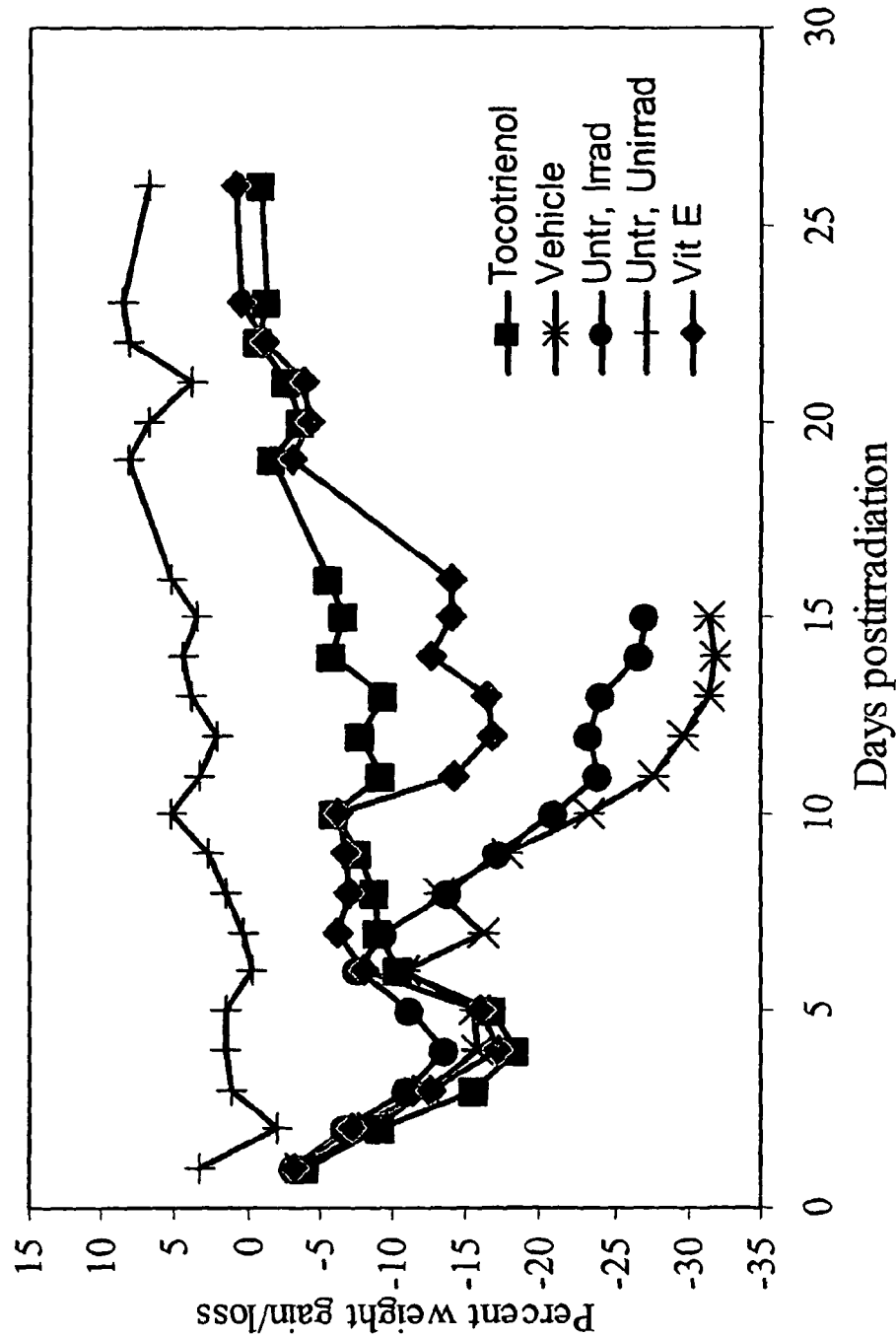
FIG. 5 shows the efficacies of γ-tocotrienol and α-tocopherol in preventing weight loss after irradiation. Mice were given α-tocopherol or tocotrienol s.c. and irradiated at 10.5 Gy with 0.6 Gy per minute.

As shown in FIG. 5, mice irradiated at 10.5 Gy lost weight in the first four days after the irradiation, and then, started to gain weight between day 4 and day 6. Among the different treatment groups, the untreated mice (Untr, Irrad) and the mice treated with vehicle (Vehicle) started to loose weight again from around day 9 and died by day 15. In contrast, mice treated with vitamin E or tocotrienol continued to gain weight and did not die from the irradiation. It should be noted, however, that mice treated with vitamin E experienced another weight loss period between day 10 and day 20.

EXAMPLE 9

Preparation of α-tocopherol Succinate (TS)

0.5 g TS (Sigma, 1210 units/g) was sonicated with 2.85 ml PEG-400 (polyethylene glycol-400) and 0.15 ml of vital-E-placebo, a solubilizing agent (Schering-Plough). The final concentration of TS in the prepared solution is 200 units/ml. At a dose of 800 unit/kg, 1 ml of the prepared solution as described above is sufficient for 8 mice. Vehicle for injection into control mice was prepared exactly as for TS except that 0.5 ml of olive oil was used instead of TS.

EXAMPLE 10

Oral Administration of α-tocopherol Succinate and Radiation

Each animal was orally administered 0.1 ml of TS solution (200 unit/ml) or vehicle by using feeding needles with a blobbed head. All administrations were done 20-24 hours before irradiation.

Animals were then placed in well-ventilated Lucite boxes (eight animals in a compartmentalized box) and irradiated in a Cobalt-60 facility at a radiation dose rate of 0.6 Gy/min for total radiation doses of 9, 9.5, and 10 Gy. The radiation doses 9.5 and 10 Gy used are lethal doses. The LD 50/30 radiation dose for this strain of animals is 8.9 Gy with the vehicle alone.

EXAMPLE 11

Radiation Protection by α-tocopherol Succinate

Figure 6:
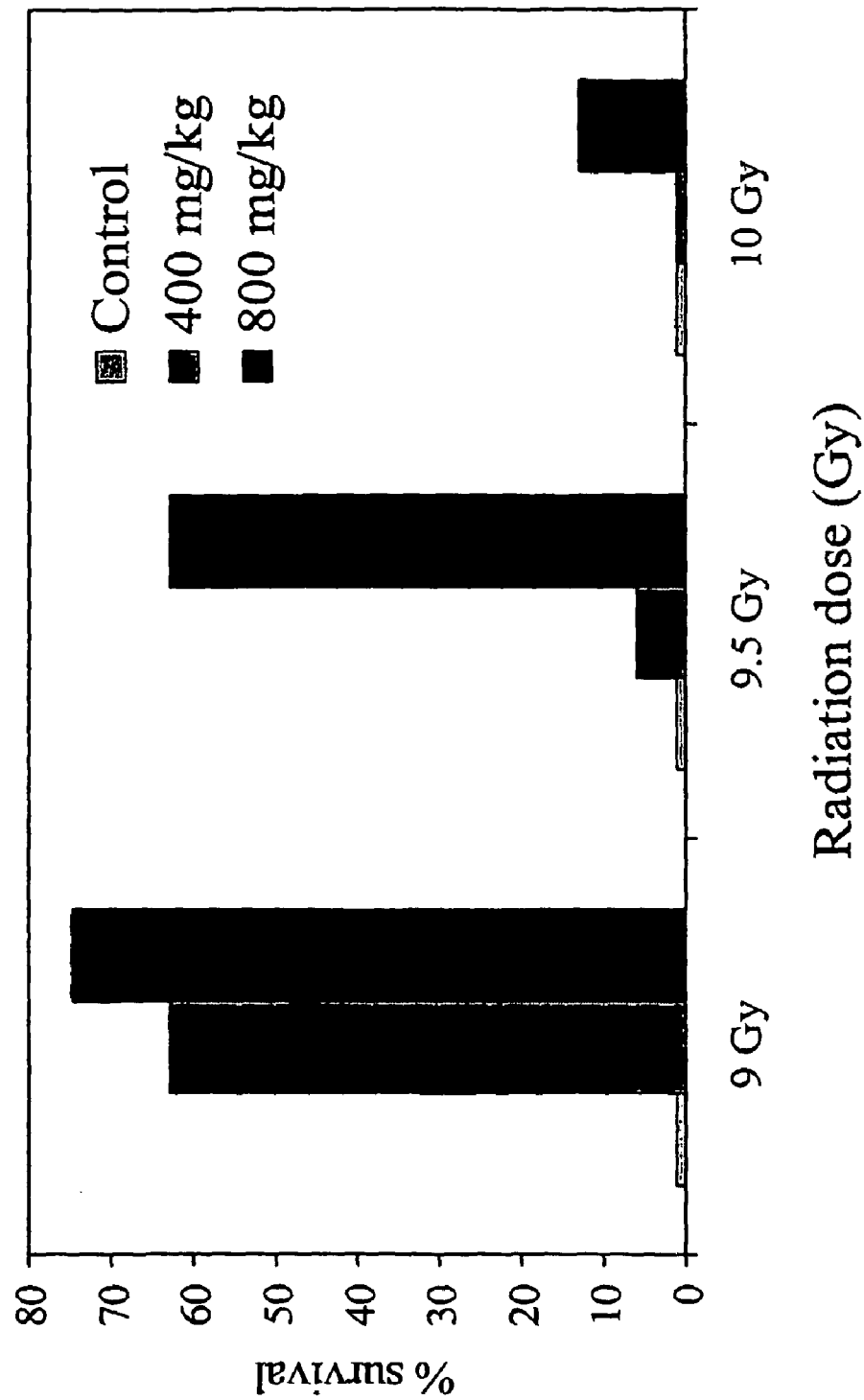
FIG. 6 shows the protection effect of orally administered α-tocopherol succinate. Survival of irradiated mice treated 400 and 800 mg/kg, p.o., with tocotrienol 24 hours before exposure to 9, 9.5 and 10 Gy cobalt-60 radiation, with 0.6 Gy per minute.

The efficacy of α-tocopherol succinate in protecting from radiation damage is monitored as described in Example 4. FIG. 6 shows that a radiation dose of 9.5 Gy kills all the control animals. However, 60% of the mice treated with α-tocopherol succinate survived at the same dose of radiation exposure.

EXAMPLE 12

Radiation Protection by γ-tocotrienol Succinate

γ-tocotrienol succinate can be synthesized by derivatization and prepared as described in Example 9 for oral administration. The effect of orally administered γ-tocotrienol succinate in radiation protection can be tested as described in Examples 10 and 4. It is anticipated that γ-tocotrienol succinate would be 40-50% more effective than α-tocopherol succinate (i.e., increase the survival rate by 40-50% under the same experimental conditions), based on the improved efficacy of γ-tocotrienol compared to α-tocopherol.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for reducing lethality in a mammal caused by exposure to a lethal dose of ionizing radiation, said method comprising:
    prior to exposure to the lethal dose of ionizing radiation administering to said mammal a therapeutically effective amount of a pharmaceutical composition consisting essentially of γ-tocotrienol in a pharmaceutically acceptable carrier, wherein the lethality to the mammal after exposure is reduced.

2. The method of claim 1, wherein γ-tocotrienol is administered subcutaneously, intramuscularly, intraperitonealy, intravascularly, or orally.

3. A method for reducing lethality in a mammal caused by exposure to a lethal dose of ionizing radiation, said method comprising:

prior to exposure to the lethal dose of ionizing radiation administering to said mammal a therapeutically effective amount of a pharmaceutical composition consisting essentially of γ-tocotrienol succinate in a pharmaceutically acceptable carrier, wherein the lethality to the mammal after exposure is reduced.

4. The method of claim 3, wherein said pharmaceutical composition is administered subcutaneously, intramuscularly, intraperitonealy, intravascularly, or orally.

5. The method of claim 1 or 3, further comprising continuing to administer to said mammal a therapeutically effective amount of the pharmaceutical composition, wherein the lethality to the mammal after exposure is reduced.

6. The method of claim 1 or 3, wherein the lethal dose of radiation is a lethal dose for humans.

7. The method of claim 1 or 3, wherein the effective dose of γ-tocotrienol or γ-tocotrienol succinate is an effective dose for humans.

8. A method for reducing lethality in a mammal caused by exposure to a lethal dose of ionizing radiation, said method comprising:

administering to said mammal a therapeutically effective amount of a pharmaceutical composition consisting essentially of isolated γ-tocotrienol or γ-tocotrienol succinate in a pharmaceutically acceptable carrier, wherein the lethality to the mammal after exposure is reduced.

9. The method of claim 8, wherein said pharmaceutical composition is administered subcutaneously, intramuscularly, intraperitonealy, intravascularly, or orally.

10. The method of claim 8, wherein the lethal dose of radiation is a lethal dose for humans.

11. The method of claim 8, wherein the effective dose of γ-tocotrienol or γ-tocotrienol succinate is an effective dose for humans.

* * * * *